United States Patent [19]

Marx et al.

[11] 4,075,233
[45] Feb. 21, 1978

[54] 16-DEHYDRO STEROIDS OF THE ANDROSTANE SERIES

[75] Inventors: Arthur Friedrich Marx, Delft; Nicolaas Cornelis Maria Emanuel Barendse, Den Hoorn, both of Netherlands

[73] Assignee: Gist-Brocades N.V., Netherlands

[21] Appl. No.: 705,446

[22] Filed: July 15, 1976

[30] Foreign Application Priority Data

July 16, 1975 United Kingdom .............. 29898/75

[51] Int. Cl.$^2$ ................................................ C07J 1/00
[52] U.S. Cl. .............................. 260/397.3; 260/397.4; 260/239.55; 260/397.5
[58] Field of Search ...................................... 260/397.3

[56] References Cited

U.S. PATENT DOCUMENTS 3,501,462 3/1970 Christiansen et al. ............ 260/239.5

OTHER PUBLICATIONS

Sondheimer et al., "J.A.C.S.", vol. 77, pp. 4145–4149.

Primary Examiner—Elbert L. Roberts
Attorney, Agent, or Firm—Robert E.. Burns; Emmanuel J. Lobato; Bruce L. Adams

[57] ABSTRACT

Therapeutically useful 16-dehydro-androstane derivatives of the general formula:

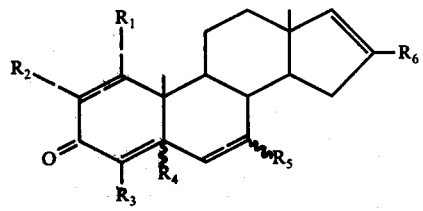

processes for their preparation and pharmaceutical compositions for the treatment of dermatological disorders, which contain as active ingredient at least one of the 16-dehydro-androstane derivatives as defined by the above formula.

44 Claims, No Drawings

16-DEHYDRO STEROIDS OF THE ANDROSTANE SERIES

This invention relates to therapeutically useful steroids of the androstane series, to processes for their preparation and to pharmaceutical compositions containing them.

The steroids of the present invention are the new 16-dehydro-androstane derivatives of the general formula:

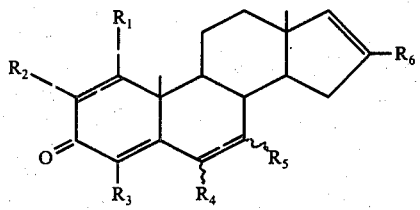

wherein $R_1$, $R_2$ and $R_5$ each represent a hydrogen atom or a methyl group or $R_1$ and $R_2$ together represent a methylene group, $R_3$ represents a hydrogen or halogen atom or a hydroxyl or methyl group, $R_4$ represents a hydrogen or halogen atom or a methyl group or $R_4$ together with $R_5$ represent a methylene group, $R_6$ represents a hydrogen atom or an alkyl group having 1 to 3 carbon atoms, the dotted lines between the 1 - 2 and the 6 - 7 positions indicate the optional presence of one or two additional double bonds, but when all the symbols R represent a hydrogen atom there is at least one double bond in one of these positions, and the waved lines in the positions 6 and 7 indicate that $R_4$ and $R_5$ each are either in α- or β-position.

Preferred compounds of general formula I are those wherein $R_1$ represents a hydrogen atom or a methyl group, $R_2$ and $R_5$ each represent a hydrogen atom, $R_3$ represents a hydrogen or halogen atom, $R_4$ represents a hydrogen or chlorine atom or a methyl group or $R_4$ and $R_5$ together represent a methylene group, $R_6$ represents a hydrogen atom or a methyl or ethyl group and also those compounds wherein a double bond is present between the 1 - 2 and/or 6 - 7 position.

Particularly preferred are those compounds of formula I wherein $R_6$ represents a hydrogen atom or a methyl or ethyl group, while the other symbols R each represent a hydrogen atom and wherein optionally one or two additional double bonds are present in the 1 - 2 and 6 - 7 positions.

Of outstanding interest are androsta-1,4,16-trien-3-one, 6α-chloro-androsta-1,4,16-trien-3-one, 1α-methyl-androsta-4,16-dien-3-one, 6α-methyl-androsta-4,16-dien-3-one, 6β-methyl-androsta-4,16-dien-3-one, 4-chloro-androsta-4,16-dien-3-one and 6β, 7β-methylene-androsta-4,16-dien-3-one, which are all within the preferred class of compounds, and also androsta-4,16-dien-3-one, which is a known compound (J.A.C.S. 77 pg 4145-49 compound VIII on pg. 4146).

Also within the scope of this invention are the 16-dehydro-androstanes according to Formula I above wherein $R_4$ represents a chlorine atom or a methyl group, the other symbols each represent a hydrogen atom or $R_4$ and $R_5$ together represent a methylene group, and wherein optionally there may be a double bond in the 1 -2 position. Similarly included are 16-dehydroandrostane derivatives wherein $R_1$ represents a methyl group and the other R symbols each represent a hydrogen atom; and the 16-dehydro-androstane derivatives wherein $R_3$ represents a chlorine atom and the other R symbols each represent a hydrogen atom.

The androstane derivatives of the general formula I androsta-4,16-dien-3-one are therapeutically useful compounds. The compounds show topical anti-androgenic activity, whereas the systemic anti-androgenic activity is very weak or absent. The compounds have a very low toxicity (acute $LD_{50}$ is mice intraperitoneally: above 1000 mg/kg) and are devoid of progesterone- and cortico-steroid-like activity and anti-gonadotrophin activity. The compounds may be used in the treatment of various dermatological disorders, including hirsutism, acne, seborrhoea, alopecia androgenetica and baldness. The 16-dehydro-androstane derivatives of general formula I may be prepared by methods known for the preparation of analogous compounds.

According to a feature of the invention, the androstane derivatives of general formula I are prepared by dehydrating in the 16-17 position a 17β-hydroxy-androstane derivative of the general formula:

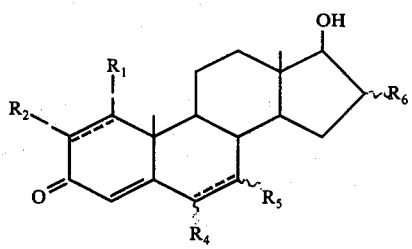

wherein $R_1$, $R_2$, $R_5$ and $R_6$ are as hereinbefore defined, $R_4$ represents a hydrogen atom or a methyl group or $R_4$ together with $R_5$ represents a methylene group and when there is a double bond in the 6–7 position, $R_4$ moreover represents a halogen atom and the waved line in position 16 indicates that the position of any 16-alkyl substituent can be in α or β configuration.

The dehydration can be carried out, for example by converting by methods known per se a 17-hydroxy-androstane derivative of the general formula II with an alkanesulphonyl halide (for example mesyl chloride) into the corresponding 17-alkanesulphonyloxy derivative. This reaction is preferably carried out in an inert organic medium in the presence of an organic base, such as pyridine. The resulting 17-alkanesulphonyloxy derivative can then be converted by heating in a suitable organic solvent, such as dimethylformamide, in the presence of lithium chloride into a 16-dehydroandrostane derivative of general formula I.

Some of the 17-hydroxy-androstane derivatives of general formula II are known compounds. A 17-hydroxy derivative of formula II, wherein $R_6$ represents an alkyl group, can be prepared by first converting a compound of the general formula:

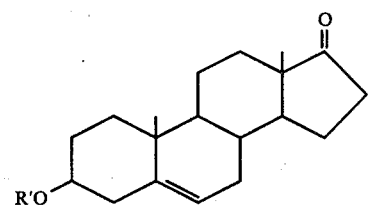

wherein R' represents a protecting group, such as the 2-tetrahydropyranyl group, into the corresponding 16-

(carboethoxy-hydroxy) methylene derivative. This conversion can be carried out by reacting a compound of formula III with diethyl oxalate in an inert organic solvent, such as benzene, in the presence of a strong base, such as sodium hydride. The 16-(carboethoxy-hydroxy) methylene derivative can then be alkylated with an alkyl iodide of the formula $R_6'I$, wherein $R_6'$ represents an alkyl group having 1 to 3 carbon atoms. This reaction is preferably carried out in a suitable solvent, such as acetone, and in the presence of a base, such as potassium carbonate. After the reaction is completed, the protecting group has to be removed again, f.e. by means of hydrochloric acid.

The $3\beta$-hydroxy-16-alkyl-androst-5-eb-17-one derivative thus obtained can then be converted in the corresponding 3-keto-$\Delta^4$ derivative.

by oxidation, for example according to the method of Oppenauer by reaction with aluminium isopropoxide in a suitable solvent, such as cyclohexanone.

The 16-alkyl-androsta-3,17-dione derivative thus obtained can then be selectively reduced to the corresponding $17\beta$-hydroxy-androstane derivative of general formula II. The reduction can be carried out, for example, by the action of sodium borohydride in methanol at a temperature below ambient, preferably between 0° and 5° C.

According to another feature of the invention the androstane derivatives of general formula I are prepared by first converting a dehydro-epi-androsterone derivative of the general formula:

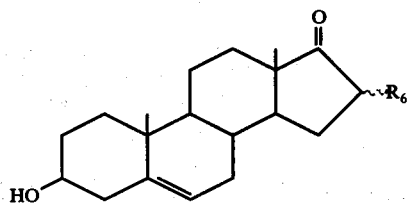

IV wherein $R_6$ is as hereinbefore defined, into a corresponding 16-dehydro derivative of the general formula:

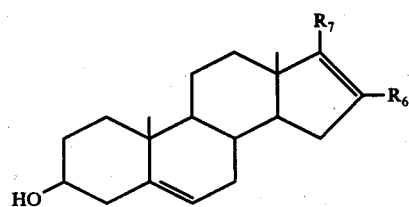

V wherein $R_6$ is as hereinbefore defined and $R_7$ represents a hydrogen or halogen atom, and converting the 16-dehydro derivative thus obtained into an androstane derivative of formula I in manner known per se.

Some of the dehydro-epi-androstane derivatives of formula IV are known compounds; the derivatives wherein $R_6$ represents an alkyl group can be obtained by alkylation of dehydro-epi-androsterone according to the process described hereinbefore.

A 16-dehydro derivative of the general formula V, wherein $R_7$ represents a chlorine atom, can be prepared by reacting the corresponding dehydro-epi-androsterone derivative of formula IV, wherein the 3-hydroxy group has been protected in conventional manner with an acyl (preferably acetyl) group, with a chlorinating agent, for example phosphorus pentachloride, in a suitable organic solvent, such as chloroform. After removing the acyl group again, there is obtained a 17-chloro-16-dehydro derivative of formula V.

In order to obtain a 16-dehydro derivative of formula V, wherein $R_7$ represents a iodine atom, a dehydro-epi-androsterone derivative of formula IV is first converted into the 17-hydrazone. This reaction is preferably carried out be refluxing a compound of formula IV with a solution of hydrazine hydrate in 96% ethanol. The 17-hydrazone derivative can then be converted into the corresponding 17-iodo derivative by reaction with iodine in an inert organic solvent, such as benzene.

A 17-halo-derivative of the general formula V obtained according to one of these processes can be converted into the corresponding 17-hydrogen derivative by reduction, for example by means of sodium and dry ethanol; then there is obtained a 16-dehydro derivative of formula V, wherein $R_7$ represents a hydrogen atom.

A 16-dehydro derivative of formula V, wherein $R_7$ represents a hydrogen atom, can also be prepared by converting a dehydro-epi-androsterone derivative of formula IV with tosylhydrazine into the corresponding 17-tosylhydrazone and removing the tosylhydrazone group again with a base, for example methyl lithium.

The 3-hydroxy-$\Delta^5$-16-dehydro derivatives of general formula V obtained according to one of these processes can be converted into the corresponding 3-keto-$\Delta^4$-16 dehydro androstane derivatives of the general formula I by oxidation, for example according to the method of Oppenauer mentioned hereinbefore, optionally followed by the introduction of one or more double bonds in the 1-2 and 6-7 positions in manner known per se.

The 16-dehydro-androstane derivatives of the general formula I obtained according to one of the processes described hereinbefore can also be used to prepare other 16-dehydro-androstane derivatives of formula I by introduction of further substituents and/or additional double bonds, as will be described hereinbelow.

According to another feature of the invention the androstane derivatives of general formula I, wherein $R_3$ represents a halogen atom or a hydroxyl group, are prepared by first converting a compound of formula I, wherein $R_3$ represents a hydrogen atom, into the corresponding 4,5-oxido derivative of the general formula:

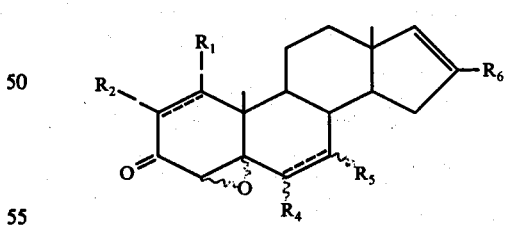

VI wherein $R_1$, $R_2$, $R_4$, $R_5$ and $R_6$ are as hereinbefore defined, for example by means of hydrogen peroxide and in an inert organic medium, such as methanol.

A 4,5-oxido derivative of formula VI thus obtained can then be converted into a corresponding 4-halo or 4-hydroxy derivative of general formula I in manner known per se.

An androstane derivative of the general formula I, wherein $R_3$ represents a halogen atom, can be obtained by reacting the corresponding 4,5-oxido derivative of formula VI with a hydrogen halogenide, for example hydrochloric or hydrobromic acid.

Androstane derivatives of general formula I, wherein $R_3$ represents a hydroxyl group, can be prepared by hydrolyzing a 4,5-oxido derivative of formula VI with a diluted mineral acid, such as sulphuric or perchloric acid.

According to still another feature of the invention the androstane derivatives of general formula I, wherein $R_4$ represents a halogen atom, are prepared by first converting a compound of formula I, wherein $R_4$ represents a hydrogen atom, into a corresponding 3-alkoxy-$\Delta^{3,5}$ derivative of the general formula:

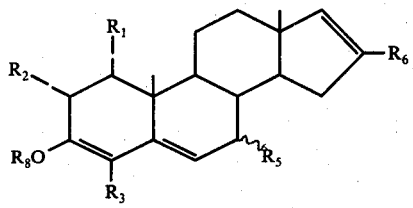

VII wherein $R_1$, $R_2$, $R_3$, $R_5$ and $R_6$ are as hereinbefore defined and $R_8$ represents a lower alkyl (preferably methyl or ethyl) group, by means of an ortho formate of the formula $HC(OR_8)_3$, wherein $R_8$ is as hereinbefore defined, in a suitable solvent, such as dioxan.

The reaction is catalyzed by acids, such as p-toluene sulphonic acid.

In order to obtain an androstane derivative of the general formula I, wherein $R_4$ represents a halogen atom, a derivative of formula VII is then reacted with a halogen amide, such as N-halo-acetamide or N-halo-succinimide, in a suitable solvent, for example acetone. The introduction of a halogen atom in position 6 is then accompanied by conversion of the 3-alkoxy-$\alpha^{3,5}$ configuration into the 3-keto-$\alpha^4$-configuration of the androstane derivatives of formula I.

This reaction usually results in 6-halo-androstane derivatives of formula I, predominantly in the $\beta$-configuration. The corresponding 6$\alpha$-halo-isomers can then be obtained by converting a 6$\beta$-halo derivative into a 3-enol ether in the manner described hereinabove and then reacting the 3-enol ether with a concentrated mineral acid, such as hydrochloric acid. In this way, the 3-alkoxy-$\Delta^{3,5}$-6-chloro derivative is converted into the corresponding 3-keto-$\Delta\alpha$-chloro-androstane derivative of formula I.

An additional double bond in the 1-2 position or 6-7 position or double bonds in both positions, can be introduced in manner known per se during various stages in the processes described hereinabove to obtain the corresponding $\Delta^1$, $\Delta^6$ or $\Delta^{1,6}$ derivatives. An additional double bond can, for example, be introduced in a 17$\beta$-hydroxy derivative of general formula II or in a 16-dehydro-androstane derivative of general formula I, wherein at least one of the 1-2 and 6-7 positions is saturated.

A double bond can be introduced in the 6-7 position by reaction with chloranil, preferably by heating in a solvent such as t-butanol in the presence of glacial acid.

A double bond in the 1-2 position can be introduced by reaction with 2,3-dichloro-5,6-dicyanobenzoquinone (DDQ) in a solvent such as benzene or dioxan or microbiologically by treatment with a suitable microorganism, such as Corynebacterium simplex.

For the introduction of double bonds in the 1-2 and 6-7 positions simultaneously, the revelant 3-keto-$\Delta^4$ compound is first converted into a corresponding 3-alkoxy-$\Delta^{3,5}$ derivative in the manner described hereinbefore. The enol-ether can then be converted into the corresponding 3-keto-$\Delta^{1,4,6}$ derivative by means of DDQ in the manner described above.

The following Examples illustrate the preparation of compounds of general formula I.

EXAMPLE I a. To a stirred solution of 20 g. of 17$\beta$-hydroxy-androsta1,4-dien-3-one in 120 ml. of dry pyridine, cooled to $-5°$ C., 12 ml. of methanesulphonyl chloride (mesyl chloride) were added in such a way that the temperature of the reaction mixture remained below 0° C. After the addition was completed, the ice bath was removed and the temperature of the reaction mixture was allowed to rise to room temperature. After completion of the reaction the mixture was poured into 1.5 l. of water, the precipitated product collected, washed with water and dried in vacuo. The crude product, 17$\beta$-mesyloxy-androsta-1,4-dien-3-one (25 g.), was not further purified but used as such.

b. A solution of 25 g. of 17$\beta$-mesyloxy-androsta-1,4-dien-3-one and 28 g. of lithium chloride in 280 ml. of dimethylformamide was heated to 130° C. under nitrogen with stirring. After 75 minutes the mixture was cooled to about 50° C. and then poured into 3 l. of water. The oily precipitate was dissolved in methyl isobutyl ketone and the organic solution concentrated to dryness in vacuo. The residue was purified by chromatography on silica gel, impregnated with silver nitrate (1600 g.SiO$_2$ containing 12% AgNO$_3$; elution with toluene + 2% acetone). The fractions containing the product were combined, washed with 25% ammonia and water. The solvent was then removed by distillation under reduced pressure and the residue crystallized from methanol. The yield was 4.3 g. of pure androsta-1,4,16-trien-3-one, m.p. 123°-125° C. mol. peak in mass spectrum (m/e): 268.

EXAMPLE II

Following the procedures described in Example I (a) and (b) 10 g. of each of the following 17$\beta$-hydroxy-androstane derivatives were converted via the corresponding androst-16-enes listed in Table I:

a. 17$\beta$-hydroxy-androsta-4,6-dien-3-one
b. 17$\beta$-hydroxy-androsta-4,6-dien-3-one
c. 17$\beta$-hydroxy-androst-4-en-3-en (testosterone)
d. 16 -methyl testosterone
e. 16$\beta$-ethyl-17$\beta$-hydroxy-androsta-1,4-dien-3-one
f. 16-isopropyl-testosterone
g. 1$\alpha$-methyl-testosterone
h. 2$\alpha$-methyl-testosterone
i. 6$\beta$-methyl-testosterone
j. 6$\alpha$-methyl-testosterone
k. 6$\beta$,7$\beta$-methylene-testosterone
l. 1$\alpha$,2$\alpha$-methylene-6-chloro-17$\beta$-hydroxyy-androsta-4,6-dien-3-one
m. 1$\alpha$,2$\alpha$-methylene-testosterone
n. 1$\alpha$,2$\alpha$-methylene-17$\beta$-hydroxy-androsta-4,6-dien-3-one
o. 6$\alpha$,7$\alpha$-methylene-testosterone
p. 4-methyl-testosterone
q. 7$\alpha$-methyl-testerone

TABLE I

| product obtained | yield in g. | melting point in °C. | mol. peak in mass spectrum (m/e) |
|---|---|---|---|
| a. androsta-4,6,16-trien-3-one | 1.3 | 122.5–124.5 | 268 |
| b. androsta-1,4,6,16-tetraen-3-one | 1.2 | 101–102 | 266 |
| c. androsta-4,16-dien-3-one | 1.3 | 131–133 | 270 |
| d. 16-methyl-androsta-4,16-dien-3-one | 2.4 | 107–108 | 284 |
| e. 16-ethyl-androsta-1,4,16-trien-3-one | 2.6 | 102–103 | 296 |
| f. 16-isopropyl-androsta-4,16-dien-3-one | 2.7 | 96–97 | 312 |
| g. 1α-methyl-androsta-4,16-dien-3-one | 1.4 | 76–77.5 | 284 |
| h. 2α-methyl-androsta-4,16-dien-3-one | 1.2 | 97–98 | 284 |
| i. 6β-methyl-androsta-4,16-dien-3-one | 1.2 | 103–104 | 284 |
| j. 6α-methyl-androsta-4,16-dien-3-one | 1.4 | 81–83 | 284 |
| k. 6β,7β-methylene-androsta-4,16-dien-3-one | 1.1 | 130–132 | 282 |
| l. 1α,2α-methylene-6-chloro-androsta-4,6,16-trien-3-one | 1.1 | 209–211 | 314 |
| m. 1α,2α-methylene-androsta-4,16-dien-3-one | 0.7 | 72–75° | 282 |
| n. 1α,2α-methylene-androsta-4,6,16-trien-3-one | 1.3 | 134–136 | 280 |
| o. 6α,7α-methylene-androsta-4,16-dien-3-one | 1.1 | 181–184 | 282 |
| p. 4-methyl-androsta-4,16-dien-3-one | 1.2 | 116–117 | 284 |
| q. 7α-methyl-androsta-4,16-dien-3-one | 1.1 | 173.5–174.5 | 284 |

EXAMPLE III a. A mixture of 10 g. of 3β-hydroxy-androst-5-en-17-one, 100 ml. of 96% ethanol, 40 ml. of triethylamine and 8 ml. of hydrazine hydrate was refluxed for 2 hours. After completion of the reaction the mixture was cooled to room temperature and poured into 700 ml. of water. The precipitate was collected, washed with water and dried. The yield of 3β-hydroxy-androst-5-en-17-one 17-hydrazone was 10.3 g. The product was crystallized from ethanol to yield the pure hydrazone melting at 214°–217° C. mol. peak in mass spectrum (m/e): 302.

b. A solution of 31.5 g. of iodine in 315 ml. of anhydrous benzene was added dropwise to a stirred suspension of 21 g. of 3βhydroxy-androst-5-en-17-one 17-hydrazone in 1.05 l. of anhydrous benzene and 0.21 l. of triethylamine. After completion of the reaction (when the added iodine solution was no longer decolourized) the mixture was cooled and then successively washed with 5% aqueous hydrogen chloride solution, water, 5% aqueous sodium hydrosulphite solution, water aqueous sodium bicarbonate solution and water. The resulting organic solution was concentrated to dryness and the residue crystallized from methanol. There were obtained 22.1 g. of pure 3β-hydroxy-17-iodo-androsta-5,16-diene, m.p. 173°–174° C. mol. peak in mass spectrum (m/e): 398.

c. 125 g. of sodium metal were added in small portions to a stirred solution of 21 g. of 3β-hydroxy-17-iodo androsta-5,16-diene in 1.05 l. of anhydrous ethanol. During the addition the mixture was kept at reflux temperature. After all of the sodium was dissolved the reaction mixture was cooled and water was added. The ethanol was removed by distillation under reduced pressure and the resulting aqueous suspension was extracted with methyl isobutyl ketone. The extract was washed until neutral and concentrated to dryness in vacuo. The crystalline residue was recrystallized from methanol-water and 13 g. of 3β-hydroxy-androsta-5,16-diene were obtained. Two crystallizations from acetone yielded the pure compound melting at 137°–138° C. mol. peak in mass spectrum (m/e): 272.

d. 250 ml. of a solution of 68 g. of 3β-hydroxy-androsta5,16-diene in 1.25 l. of toluene and 0.5 l. of cyclohexanone was distilled to obtain an anhydrous solution. A solution of 34 g. of aluminum isopropoxide in 170 ml. of dry toluene was added. The mixture was slowly distilled during 30 minutes to remove the acetone formed. After completion of the reaction water was added, and the mixture steam distilled to remove volatile components. the residue was extracted with methyl isobutyl ketone and the extract washed with an aqueous hydrogen chloride solution and water. The solvent was removed by distillation in vacuo and the residue was crystallized from acetone; 38.1 g. of androsta-4,16-dien-3-one were obtained. Recyrstallization from acetone yielded a pure product melting at a 131°–133° C. mol. peak in mass spectrum (m/e):

EXAMPLE IV a. To a stirred solution of 23 g. of 3β(2'-tetrahydropyranyloxy)-androst-5-en-17-one (the tetrahydropyranyl ether of dehydro-epi-androsterone) in 630 ml. of benzene and 31.5 ml. of diethyl oxalate, 10.5 g. of sodium hydride (50% suspension in mineral oil) were added in portions, under nitrogen. After the addition the mixture was stirred overnight under nitrogen at room temperature. Excess reagent was then decomposed by the addition of 8 ml. of anhydrous ethanol and the mixture was poured into 420 ml. of water containing 8 ml. of acetic acid. The organic layer was separated and the water phase extracted twice with benzene. The extracts were combined, washed well with water and concentrated under reduced pressure to about 50 ml. Upon the addition of 150 ml. of heptane the product crystallized. The crystals were collected and dried in vacuo. The yield was 21 g. of 3β-(2'-tetrahydropyranyloxy)-16-(carboethoxy-hydroxy)methylene-androst-5-en-17-one, m.p. 124°–125° C.

b. 5 g. of the above mentioned product were dissolved in 100 ml. of acetone. To this solution 5 g. of powdered potassium carbonate and 5 ml. of methyl iodide were added and the mixture was heated to reflux. After 21 hours the reaction mixture was cooled and concentrated in vacuo. The residue was treated with water and extracted with methyl isobutyl ketone. The organic extract was evaporated to dryness under reduced pressure. To the residue a freshly prepared solution of 0.5 g. of sodium in 50 ml of anhydrous ethanol was added and the mixture was refluxed for 30 minutes. The solvent was then evaporated, the residue treated with water and extracted with methyl isobutyl ketone. The extract was concentrated, and the residue dissolved in 50 ml. of boiling methanol. To this solution 3 ml. of 2 N hydrochloric acid were added and the mixture was refluxed for 30 minutes and then set aside for 2 hours at room temperature. The reaction mixture was concentrated under reduced pressure and after the addition of water to the residue, the product crystallized. The crystals were collected, washed with cold methanol and dried. The product was recrystallized from acetone yielding 1.6 g. of pure 3$\beta$-hydroxy-16$\xi$-methyl-androst-5-en-17-one; m.p. 167°-170° C. mol. peak in mass spectrum (m/e): 302. (c) Following the procedures described in Example III (a), (b), (c) and (d) 10 g. of 3$\beta$-hydroxy-16$\xi$-methyl-androst-5-en-17-one were converted into 3.5 g. of 16-methyl androsta-4,16-dien-3-one, m.p. 107°-108° C. mol. peak in mass spectrum (m/e): 284.

EXAMPLE V a. Following the procedures described in Example IV (a) and (b) 10 g. of 3$\beta$-(2'-tetrahydropyranyloxy)-androst-5-en-17-one were converted via 3$\beta$-(2'-tetrahydropyranyloxy)-16-(carboethoxy-hydroxy)methylene-androst-5-en-17-one into 3 g. of 3$\beta$-hydroxy-16$\xi$-ethyl-androst-5-en-17-one, m.p. 152°-155° C. mol. peak in mass spectrum (m/e): 316.

b. Following the procedures described in Example III (a), (b), (c) and (d) 10 g. of 3$\xi$-hydroxy-16$\xi$-ethyl-androst-5-en-17-one were converted into 3.1 g. of 16-ethyl androsta-4,16-dien-3-one, m.p. 104°-105.5° C. mol. peak in mass spectrum (m/e): 298

EXAMPLE VI a. Following the procedures described in Example IV (a) and (b) 10 g. of 3$\beta$(2'-tetrahydropyranyloxy)-androst-5-en-17-one were converted via its 16-(carboethoxy-hydroxy) methhylene derivative into 1.2 g. of 3$\beta$-hydroxy-16$\xi$-isopropyl-androst-5-en-17-one, m.p. 117°-120° C. mol. peak in mass spectrum (m/e): 330.

b. Following the procedures described in Example III (a), (b), (c) and (d) 10 g. of 3$\beta$-hydroxy-16$\xi$-isopropyl-androst-5-en-17-one were converted into 2.8 g. of 16-isopropyl-androsta-4,16-dien-3-one, m.p. 96°-97° C. mol. peak in mass spectrum (m/e): 312.

EXAMPLE VII

To a solution of 2.9 g. of 3$\beta$-hydroxy-androst-5-en-17-one in 200 ml. of methanol were added 1.7 g. of tosyl hydrazine and 3 drops of concentrated sulphuric acid, and the mixture was refluxed for 3 hours under nitrogen. The resulting solution was concentrated under reduced pressure amd the crystallized product collected and dried in vacuo to give 3.0 g. of the 17-tosyl hydrazone. A solution of this material in 150 ml. of anhydrous tetrahydrofuran was cooled to 0°-5° C. and 30 ml. of a 2.4 molar methyl lithium solution were added. The mixture was kept under nitrogen at room temperature for 48 hours. The mixture was then cooled, diluted with ice-water, acidified and several times extracted with diethyl ether. The extract was successively washed with 10% aqueous sodium bicarbonate solution, water, saturated sodium chloride solution and dried over magnesium sulphate. The solvent was removed and the residue crystallized from acetone: yield 2.0 g. of 3$\beta$-hydroxy-androsta-5,16-diene, m.p. 137°-138° C. mol. peak in mass spectrum (m/e): 272.

This product was further converted to androsta-4,16-dien-3-one in the manner described in Example III (d).

EXAMPLE VIII a. 29.2 g. of phosphorus pentachloride were added to a stirred and cooled solution of 23 g. of 3$\beta$-acetoxy-androst-5-en-17-one in 105 ml. of dry chloroform. After 0.75 hours the reaction mixture was poured with stirring into a cooled mixture of 1 l. of methyl isobutyl ketone and 44.8 g. of sodium hydroxide pellets dissolved in 350 ml. of water. The organic layer was separated, washed three times with water and concentrated under reduced pressure. The residue was crystallized from acetone yielding 6.9 g. of 3$\beta$-acetoxy-17-chloro-androsta-5,16-diene, m.p. 167°-169.5° C.

This product was dissolved in 350 ml. of boiling methanol; 3.2 g. of sodium hydroxide pellets were added and the mixture was refluxed for 10 minutes. Next 175 ml. of water were added and the mixture was cooled in an ice bath. The product which crystallized was removed by filtration, washed with 70% methanol and dried in vacuo. Recrystallization of the product from methanol yielded 3.8 g. of pure 3$\beta$-hydroxy-17-chloro-androsta-5,16-diene, m.p. 145°-147° C.

mol. peak in mass spectrum (m/e): 306.

b. Following the procedures described in Example III c. and d. 3$\beta$-hydroxy-17-chloro-androsta-5,16-diene was converted into adrosta-4,16-dien-3-one

EXAMPLE IX a. 90 ml. of 31% hydrogen peroxide and 36 ml. of 10% aqueous sodium hydroxide were successively added dropwise to a stirred suspension of 22.5 g. of androsta-4,16-dien-3-one. in 560 ml. of methanol at room temperature. After 2 hours the conversion was complete and the reaction mixture was poured into 1 l. of water. The crystalline product was filtered off, washed with water and dried. Crystallization from methanol yielded 10.9 g. of pure 4$\alpha$, 5$\alpha$-oxido-androst-16-en-3-one m.p. 117°-118° C.

mol. peak in mass spectrum (m/e): 286.

b. To a solution of 2.3 g of 4$\alpha$, 5$\alpha$-oxido-androst-16-en-3-one in 23 ml. of acetone, 2.3 ml. of 36% hydrochloric acid were added. After 20 minutes the reaction mixture was poured into a 1 molar aqueous sodium bicarbonate solution. The crude product was purified by chromatography on a silicagel column (Merck "Fertigsaule", size C; elution with toluene). The fractions containing the product were combined and the solvent was evaporated under reduced pressure. The residue was crystallized from methanol. The yield was 1.2 g. of pure 4-chloro-androsta-4,16-dien-3-one, m.p. 123°-125° C.

mol. peak in mass spectrum (m/e): 304.5.

EXAMPLE X

Following the procedure described in Example IX (b) 5 g. of 4$\alpha$, 5$\alpha$-oxido-androst-16-en-3-one were converted with hydrobromic acid into 3.8 g. of 4-bromo-androsta-4,16-dien-3-one, m.p. 130°-131° C.

mol. peak in mass spectrum (m/e): 349.

EXAMPLE XI

To a stirred solution of 5 g. of 4$\alpha$, 5$\alpha$-oxido-androst-16-en-3-one (prepared according to the procedure described in Example IX (a)) in 50 ml. of propionic acid were added 5 ml. of concentrated sulphuric acid. After 5 minutes the reaction mixture was poured into 1 l. of a 2 molar aqueous sodium bicarbonate solution. The crystals were filtered off, washed well with water and dried.

The product was purified by chromatography on a silicagel column (100 g. of silicagel; elution with toluene). The matching fractions were combined and the solvent removed by distillation under reduced pressure. The residue was crystallized from acetone. The yield was 1.2 g. of pure 4-hydroxy-androsta-4,16-dien-3-one, m.p. 154°–156° C.

mol. peak in mass spectrum (m/e): 286.

EXAMPLE XII a. A mixture of 60 ml. of dioxan, 6 ml. of triethyl orthoformate and 0.3 g. of p-toluene sulphonic acid monohydrate was stirred at room temperature. After 30 minutes 6 g. of androsta-4,16-dien-3-one and 6 ml. of triethyl orthoformate were added and the resulting mixture was stirred for an additional hour at room temperature after which the conversion was complete. 1 ml. of pyridine was added and the mixture was then poured into 500 ml. of water. The product was filtered off, washed with water and dried. Crystallisation from ethanol containing 0.1% pyridine yielded 5.4 g. of pure 3-ethoxy-androsta-3,5,16-triene, m.p. 108°–109° C.

mol. peak in mass spectrum (m/e): 298.

b. A solution of 3 g. of 3-ethoxy-androsta-3,5,16-triene and 2.4 g. of N-chloro-succinimide in 25 ml. of acetone and 5 ml. of water for 25 minutes at room temperature. Thereafter 16 ml. of a 0.5 molar aqueous sodium sulphite solution were added and the reaction mixture was then diluted with 250 ml. of water and extracted with methylene chloride. The extract was washed successively with a molar aqueous sodium carbonate solution and water and then evaporated to dryness. The residue was crystallized from methanol-water yielding 2.4 g. of pure 6$\beta$-chloro-androsta-4,16-dien-3-one, m.p. 96°–98° C.

mol. peak in mass spectrum (m/e): 304.5.

EXAMPLE XIII

Following the procedure described in Example XII (b) 3 g. of 3-ethoxy-androsta-3,5,16-triene were converted with N-bromo-succinimide into 1.9 g. of pure 6$\beta$-bromo-androsta-4,16-dien-3-one, m.p. 112°–113° C./ mol. peak in mass spectrum (m/e)- 349.

EXAMPLE XIV

Following the procedure described in Example XII (b) 3 g. of 3-ethoxy-androsta-3,5,16-triene were converted with N-iodo-succinimide into 2.5 g. of pure 6$\beta$-iodo-androsta-4,16-dien-3-one, m.p. 88°–89° C.

mol. peak in mass spectrum (,/e): 396.

EXAMPLE XV

Following the procedures described in Example XII (a) and (b) 2.5 g. of 16-methyl-androsta-4,16-dien-3-one (prepared according to the procedure described in Example II (d)) were converted into 2.0 g. of 6$\beta$-chloro-16-methyl-androsta-4,16-dien-3-one m.p. 119°–123° C.

mol. peak in mass spectrum (m/e): 318.5.

EXAMPLE XVI

Following the procedures described in Example XII (a) and (b) 2.5 g. of 1$\alpha$-methyl-androsta-4,16-dien-3-one (prepared according to the procedure described in Example II (g)) were converted into 1.9 g. of 1$\alpha$-methyl-6$\beta$-chloro-androsta-4,16-dien-3-one, obtained as an oil. NMR ($\delta$ in CDCl$_3$): 0.87, 0.91 (doublet), 1.56, 4.78 (doublet) 5.80 (multiplet), 5.89 p.p.m.

mol. peak in mass spectrum (m/e): 318.

EXAMPLE XVII a. Following the procedure described in Example XII (a) 4 g. of 6$\beta$-chloro-androsta-4,16-dien-3-one (prepared according to the procedure described in Example XII (b)) were converted into 2.4 g. of 3-ethoxy-6-chloro-androsta-3,5,16-triene, m.p. 111°–111, 5° C.

mol. peak in mass spectrum (m/e): 332.5.

b. 2.4 g. of 3-ethoxy-6-chloro-androsta-3,5,16-triene were added to a solution of 1.25 ml. of concentrated hydrochloric acid in 50 ml. of acetone prewarmed to 50° C. After the addition the mixture was kept for an additional 10 minutes at 50° C. and thereafter cooled in ice and neutralized with 40 ml. of 0.5 molar aqueous solution of ammonium acetate. Upon addition of 40 ml. of water the product crystallized. The product was purified by chromatography (Merck "Fertigsaule", SiO$_2$ 60C elution with benzene + 1% acetone). The fractions containing the product were combined and the solvent was evaporated. The residue was crystallized from acetone-water. The yield was 1.5 g. of 6$\alpha$-chloro-androsta-4,16-dien-3-one, m.p. 148°–150° C.

mol. peak in mass spectrum (m/e): 304.5.

EXAMPLE XVIII

Following the procedures described in Example XVII (a) and (b) 3.6 g. of 6$\beta$-bromo-androsta-4,16-dien-3one (prepared according to the procedure described in Example XIII) were converted into 0.9 g. of 6$\alpha$-bromo-androsta-4,16-dien-3-one, m.p. 133°–133.5° C.

mol. peak in mass spectrum (,/e): 349.

EXAMPLE XIX

Following the procedures described in Example XVII (a) and (b) 3 g. of 1$\alpha$-methyl-6$\beta$-chloro-androsta-4,16-dien-3-one (prepared according to the procedure described in Example XVI) were converted into 1.2 g. of 1$\alpha$-methyl-6$\alpha$-chloro-androsta-4,16-dien-3-one, m.p. 157.5°–158° C.

mol. peak in mass spectrum (m/e): 318.

EXAMPLE XX

Following the procedures described in Example XVII (a) and (b) 3 g. of 6$\beta$-chlorio-16-methyl-androsta-4,16-dien-3-one (prepared according to the procedure described in Example XV) were converted into 6$\alpha$-chloro-16-methyl-androsta-4,16-dien-3-one, m.p. 186°–187° C.

mol. peak in mass spectrum (m/e): 318.5.

EXAMPLE XXI 7.7 g. of 6$\alpha$-chloro-androsta-4,16-dien-3-one (prepared according to the procedure described in Example XVII) and 8.4 g. of 2,3-dichloro-5,6-dicyano benzoquinone were dissolved in 100 ml. of anhydrous dioxan and the mixture was heated to reflux. After refluxing for 3 hours the conversion was complete and the reaction mixture was cooled in ice. The crystallized dichloro-dicyano-hydroquinone was filtered off and washed with methylene chloride. The filtrate and washings were combined and evaporated to dryness. The residue was dissolved in benzene and chromatographed on a silica-gel column (Merck Fertigsaule, "SiO$_2$ C; elution with benzene containing 1.5% acetone). The fractions containing the product were combined and the solvent was distilled under reduced pressure. The residue was crystallized from methanol. The yield was 1.7 g. of pure 6α-chloro-androsta-1,4,16-trien-3-one, m.p. 148°–149° C.

mol. peak in mass spectrum (m/e): 302.5.

EXAMPLE XXII

Following the procedure described in Example XXI 5 g. of androsta-4,16-dien-3-one were converted into 2.5 g. of androsta-1,4,16-trien-3-one, m.p. 123°–125° C.

mol. peak in mass spectrum (m/e): 268.

EXAMPLE XXIII

A mixture of 5.4 g. of androsta-4,16-dien-3-one 14.8 g. of chloranil, 600 ml. of t-butanol and 10 ml. of acetic acid was refluxed for 3 hours. It was then cooled to room temperature and the crystallized tetrachloro-hydroquinone was filtered off and washed with t-butanol. The filtrate and washings were combined and evaporated to dryness. The residue was treated with toluene (200 ml.), filtered and the toluene solution was washed three times with a 15% aqueous solution of sodium hydroxide and with water toneutrality. The toluene solution was concentrated to dryness and the residue crystallized successively from methanol, benzene and heptane. The yield was 2.4 g. of androsta-4,6,16-trien-3-one, m.p. 122.5°–124° C. mol. peak in mass spectrum (m/e): 268.

Example XXIV 5 g. of 3-ethoxy-androsta-3,5,16-triene, (prepared according to the procedure described in Example XII (a)) were dissolved in 50 ml. of anhyrous dioxan. To this solution 4.6 g. of 2,3-dichloro-5,6-dicyano benzoquinone were added and the mixture was stirred for an additional 5 minutes at room temperature. The precipitated dichloro-dicyano-hydroquinone was then filtered off and washed well with methylene chloride. The filtrate and washings were combined and evaporated to dryness. The residue was purified on a silicagel column (100 g. SiO$_2$, elution with benzene containing 1.5% acetone). The matching fractions were combined and the solvent evaporated. The residue was crystallized from methanol yielding 1.5 g. of androsta-1,4,6,16-tetraen-3-one, m.p. 100.5°–102° C. mol peak in mass spectrum (m/e): 266.

The 16-dehydro-androstane derivatives of general formula I and androsta-1,4-dien-3-one may be used as anti-androgenic agents in humans and animals. The daily dose and preferred concentration vary depending on the route of administration. For therapeutic purposes individual or mixtures of the compounds may be employed in the form of pharmaceutical preparations customarily employed for administration of therapeutically active substances. The invention therefore provides pharmaceutical compositions comprising, as the active ingredient, one or more of the compounds of general formula I in association with a pharmaceutically acceptable carrier. Pharmaceutical compositions comprising androsta-1,4,16-trien-3-one, 1α-methyl-androsta-4,16-dien-3-one, 4-chloro-androsta-4,16-dien-3-one, 6β-methyl-androsta-4,16-dien-3-one, 6α-methyl-androsta-4,16-dien-3-one, 6α-chloro-androsta-1,4,16-trien-3-one, 6β,7β-methylene-androsta-4,16-dien-3-one and androsta-1,4-dien-3-one individually or in combination with each other are particularly preferred.

The compounds of formula I are preferably administered topically. Preferred pharmaceutical compositions are accordingly those suitable for topical use such as gels, lotions, creams, ointments, sticks and emulsions.

The preferred concentration of the active ingredient in compositions for topical administration is 0.01 to 10% by weight.

The active substance may also be made up in a form suitable for parenteral administration, i.e. as a solution or as a suspension or emulsion in an organic liquid usually employed for injectable preparations, for example a vegetable oil such as olive oil. Compositions for parenteral administration such as solutions or suspensions preferably contain from 5 to 250 mg./ml. and the preferred daily dosage is from 1 to 5 ml.

For veterinaary use parenteral administration is preferred. Veterinary compositions for parenteral administration preferably contain 1 to 100 mg./ml. and the preferred daily dosage is from 1 to 10 ml.

The following Examples illustrate the preparation of pharmaceutical compositions according to the present invention.

EXAMPLE XXV

A gel was prepared from the following ingredients:-

| | | |
|---|---|---|
| androsta-1,4,16-trien-3-one | | 2 g. |
| ethyl alcohol | | 70 g. |
| propylene glycol | | 8 g. |
| Carbopol 940® | | 1 g. |
| diisopropanolamine | | 1 g. |
| water | q.s.p. | 100 ml. |

EXAMPLE XXVI

A lotion was prepared from the following ingredients:-

| | |
|---|---|
| 6α-chloro-androsta-1,4,6-trien-3-one | 2 g. |
| ethyl alcohol | 49 g. |
| polyethylene glycol | 49 g. |

EXAMPLE XXVII

A stick for local application was prepared from the following ingredients:-

| | |
|---|---|
| 4-chloro-androsta-4,16-dien-3-one | 2 g. |
| ethyl alcohol | 80 g. |
| perfume oil | 1.4 g. |
| sodium stearate | 6 g. |
| glycerol | 2.6 g. |
| propylene glycol | 3 g. |
| water | 5 g. |

EXAMPLE XXVIII

A gel was prepared from the following ingredients:-

| | | |
|---|---|---|
| androsta-4,16-dien-3-one | | 2 g. |
| ethyl alcohol | | 70 g. |
| propylene glycol | | 8 g. |
| Carbopol 940® | | 1 g. |
| diisopropanolamine | | 1 g. |
| water | q.s.p. | 100 ml. |

What we claim is:

1. 16-Dehydro-androstane derivatives of the general formula:

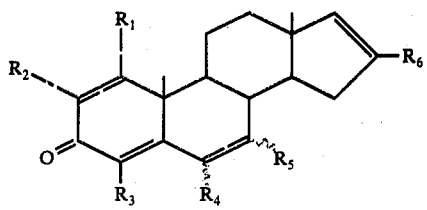

wherein $R_1$, $R_2$ and $R_5$ each represent a hydrogen atom or a methyl group or $R_1$ and $R_2$ together represent a methylene group, $R_3$ represents a hydrogen or halogen atom or a hydroxyl or methyl group, $R_4$ represents a hydrogen or halogen atom or a methyl group or $R_4$ together with $R_5$ represent a methylene group, $R_6$ represents a hydrogen atom or an alkyl group having 1 to 3 carbon atoms, the dotted lines between the 1 - 2 and the 6 - 7 positions indicate the optional presence of one or two additional double bonds, but when all the symbols R represent a hydrogen atom there is at least one double bond in one of these positions, and the waved lines in the positions 6 and 7 indicate that $R_4$ and $R_5$ each are either in $\alpha$- or $\beta$-position.

2. 16-Dehydro-androstane derivatives according to claim 1, wherein $R_1$ represents a hydrogen atom or a methyl group, $R_2$ and $R_5$ each represent a hydrogen atom, $R_3$ represents a hydrogen or halogen atom, $R_4$ represents a hydrogen or chlorine atom or a methyl group or $R_4$ and $R_5$ together represent a methylene group, $R_6$ represents a hydrogen atom or a methyl or ethyl group and/or a double bond is present between the 1–2 and/or 6–7 position.

3. 16-Dehydro-androstane derivatives according to claim 1, wherein $R_6$ represents a hydrogen atom or a methyl or ethyl group, while the other symbols R each represent a hydrogen atom and wherein optionally one or two additional double bonds are present in the 1-2 and 6-7 positions.

4. 16-Dehydro-androstane derivatives according to claim 1, wherein $R_4$ represents a chlorine atom or a methyl group, the other symbols R each represent a hydrogen atom or $R_4$ and $R_5$ together represent a methylene group, and wherein optionally a double bond is in the 1–2 position.

5. 16-Dehydro-androstane derivatives according to claim 1, wherein $R_1$ represents a methyl group and the other symbols R each represents a hydrogen atom.

6. 16-Dehydro-androstane derivatives according to claim 1, wherein $R_3$ represents a chlorine atom and the other symbols R each represent a hydrogen atom.

7. The androstane derivative according to claim 1, Androstrat-1,4,16-trien-3-one.

8. The androstane derivative according to claim 1, Androsta-4,6,16-trien-3-one.

9. The androstane derivative according to claim 1, Androsta-1,4,6,16-tetraen-3-one.

10. The androstane derivative according to claim 1, 16-Methyl-androsta-4,16-dien-3-one.

11. The androstane derivative according to claim 1, 16-Ethyl-androsta-1,4,16-trien-3-one.

12. The androstane derivative according to claim 1, 16-Isopropyl-androsta-4,16-dien-3-one.

13. The androstane derivative according to claim 1, 1α-Methyl-androsta-4,16-dien-3-one.

14. The androstane derivative according to claim 1, 2α-Methyl-androsta-4,16-dien-3-one.

15. The androstane derivative according to claim 1, 6β-Methyl-androsta-4,16-dien-3-one.

16. The androstane derivative according to claim 1, 6α-Methyl-androsta-4,16-dien-3-one.

17. The androstane derivative according to claim 1, 6β,7β-Methylene-androsta-4,16-dien-3-one.

18. The androstane derivative according to claim 1, 1α,2α-Methylene-6-chloro-androsta-4,1, 16-trien-3-one.

19. The androstane derivative according to claim 1, 16-Ethyl-androsta-4,16-dien-3-one.

20. The androstane derivative according to claim 1, 4-Chloro-androsta-4,16-dien-3-one.

21. The androstane derivative according to claim 1, 4-Bromo-androsta-4,16-dien-3-one.

22. The androstane derivative according to claim 1, 4-Hydroxy-androsta-4,16-dien-3-one.

23. The androstane derivative according to claim 1, 6β-Chloro-androsta-4,16-dien-3-one.

24. The androstane derivative according to claim 1, 6β-Bromo-androsta-4,16-dien-3-one.

25. The androstane derivative according to claim 1, 6β-Indo-androsta-4,16-dien-3-one.

26. The androstane derivative according to claim 1, 6β-Chloro-16-methyl-androsta-4,16-dien-3-one..

27. The androstane derivative according to claim 1, 1α-Methyl-6βchloro-androsta-4,16-dien-3-one.

28. The androstane derivative according to claim 1, 6α-Chloro-androsta-4,16-dien-3-one.

29. The androstane derivative according to claim 1,6α-Bromo-androsta-4,16-dien-3-one.

30. The androstane derivative according to claim 1, 1α-Methyl-6α-chloro-androsta-4,16-dien-3-one.

31. The androstane derivative according to claim 1, 6α-Chloro-16-methyl-androsta-4,16-dien-3-one.

32. The androstane derivative according to claim 1, 6α-Chloro-androsta-1,4,16-trien-3-one.

33. The androstane derivative according to claim 1, 1α,2β-Methylene-androsta-4,16-dien-3-one.

34. The androstane derivative according to claim 1, 1α,2α-methylene-androsta-4,6,16-trien-3-one.

35. The androstane derivative according to claim 1, 6α,7α-Methylene-androsta-4,16-dien-3-one.

36. The androstane derivative according to claim 1, 4-Methyl-androsta-4,16-dien-3-one.

37. The androstane derivative according to claim 1, 7α-Methyl-androsta-4,16-dien-3-one.

38. A process for preparing the 16-dehydroandrostane derivatives as claimed in claim 1, which comprises converting a 17β-hydroxy-androstane derivative of the general formula:

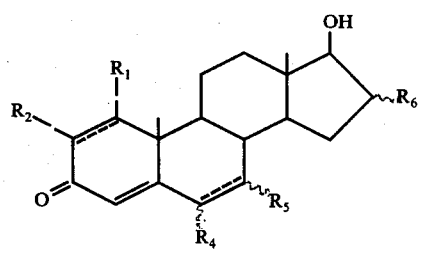

wherein $R_1$, $R_2$, $R_5$ and $R_6$ are as defined in claim 1, $R_4$ represents a hydrogen atom or a methyl group or $R_4$ together with $R_5$ represent a methylene group and when there is a double bond in the 6-7 position, $R_4$ moreover represents a halogen atom and the waved line in position 16 indicates that the position of any 16-alkyl substituent can be in α or β configuration, with an alkanesulphonyl halide into the corresponding 17-alkanesulphonyloxy derivative, and heating this compound in an organic medium in the presence of lithium chloride to obtain a 16-dehydro-androstane derivative of formula I in claim 1, wherein $R_1R_2$, $R_4$, $R_5$ and $R_6$ are as hereinbefore defined.

39. Process according to claim 38, wherein the alkanesulphonyl halide is mesyl chloride.

40. Process for preparing androsta-4,16-dien-3-one, which comprises converting 17β-hydroxy-androst-4-en-3-one with an alkanesulphonyl halide into 17β-alkanesulphonyoxy-androst-4-en-3-one and heating this compund in an organic medium in the presence of lithium chloride.

41. Process according to claim 40, wherein the alkanesulphonyl halide is mesyl chloride.

42. Pharmaceutical compositions for the topical treatment of dermatological disorders which comprise as an active agent at least one of the 16-dehydroandrostane derivatives as claimed in claim 1, in admixture with a pharmaceutical carrier for topical application.

43. Pharmaceutical compositions according to claim 42 wherein the active agent is selected from the group consisting of androsta-1,4,16-trien-3-one,1α-methyl-androsta-4,16-dien-3-one, 6α-methyl-androsta-4,16-dien-3-one, 6β-methyl-androsta-4,16-dien-3-one, 4-chloro-androsta-4,16-dien-3-one, 6β,7β-methylene-androsta-4,16-dien-3-one and 6α-chloro-androsta-1,4,16-trien-3-one.

44. Pharmaceutical compositions for the treatment of dermatological disorders which comprise as an active ingredient androsta-4,16-dien-3-one in admixture with a pharmaceutical topical carrier.

* * * * *